(12) United States Patent
Brumbach et al.

(10) Patent No.: US 6,613,056 B1
(45) Date of Patent: Sep. 2, 2003

(54) ULTRASONIC PROBE WITH LOW-FRICTION BUSHINGS

(75) Inventors: John C. Brumbach, Chicago, IL (US); Dennis Hechel, Gurnee, IL (US)

(73) Assignee: Misonix, Inc., Farmingdale, NY (US)

( * ) Notice: Subject to any disclaimer, the term of this patent is extended or adjusted under 35 U.S.C. 154(b) by 0 days.

(21) Appl. No.: 09/251,791

(22) Filed: Feb. 17, 1999

(51) Int. Cl.⁷ ............................................... A61B 17/22
(52) U.S. Cl. ..................................................... 606/128
(58) Field of Search .............................. 601/2; 606/127, 606/128

(56) References Cited

U.S. PATENT DOCUMENTS

| | | | |
|---|---|---|---|
| 3,956,826 A | * 5/1976 | Perdreaux, Jr. | ........... 128/24 A |
| 4,237,871 A | 12/1980 | Bonnet | |
| 4,279,245 A | 7/1981 | Takagi et al. | |
| 4,336,794 A | 6/1982 | Chikama | |
| 4,431,006 A | * 2/1984 | Trimmer et al. | ........... 128/660 |
| 4,561,446 A | 12/1985 | Hetz | |
| 4,875,468 A | 10/1989 | Krauter et al. | |
| 4,984,563 A | 1/1991 | Renaud | |
| 5,123,903 A | * 6/1992 | Quaid et al. | ................... 604/22 |
| 5,151,084 A | 9/1992 | Khek | |
| 5,242,385 A | * 9/1993 | Strukel | ......................... 604/22 |
| 5,354,265 A | * 10/1994 | Mackool | ..................... 606/128 |
| 5,397,293 A | 3/1995 | Alliger et al. | |
| 5,437,678 A | * 8/1995 | Sorensen | ..................... 606/107 |
| 5,486,162 A | 1/1996 | Brumbach | |
| 5,488,955 A | 2/1996 | Dias | |
| 5,722,980 A | * 3/1998 | Schulz et al. | ................ 606/128 |
| 5,741,272 A | * 4/1998 | Kuhne | ......................... 606/128 |
| 5,817,014 A | * 10/1998 | Hori et al. | ................... 600/118 |
| 5,868,756 A | * 2/1999 | Henry et al. | ................. 606/128 |
| 5,906,623 A | * 5/1999 | Peterson | ..................... 606/128 |

* cited by examiner

*Primary Examiner*—Eduardo C. Robert
(74) *Attorney, Agent, or Firm*—Welsh & Katz, Ltd.

(57) ABSTRACT

An ultrasonic probe assembly is provided. The probe assembly includes a cannula and an ultrasonic probe disposed within the cannula. The probe assembly further includes a low-friction bushing disposed within the cannula and adapted to maintain the cannula and ultrasonic probe in a relatively fixed longitudinal relationship.

15 Claims, 2 Drawing Sheets

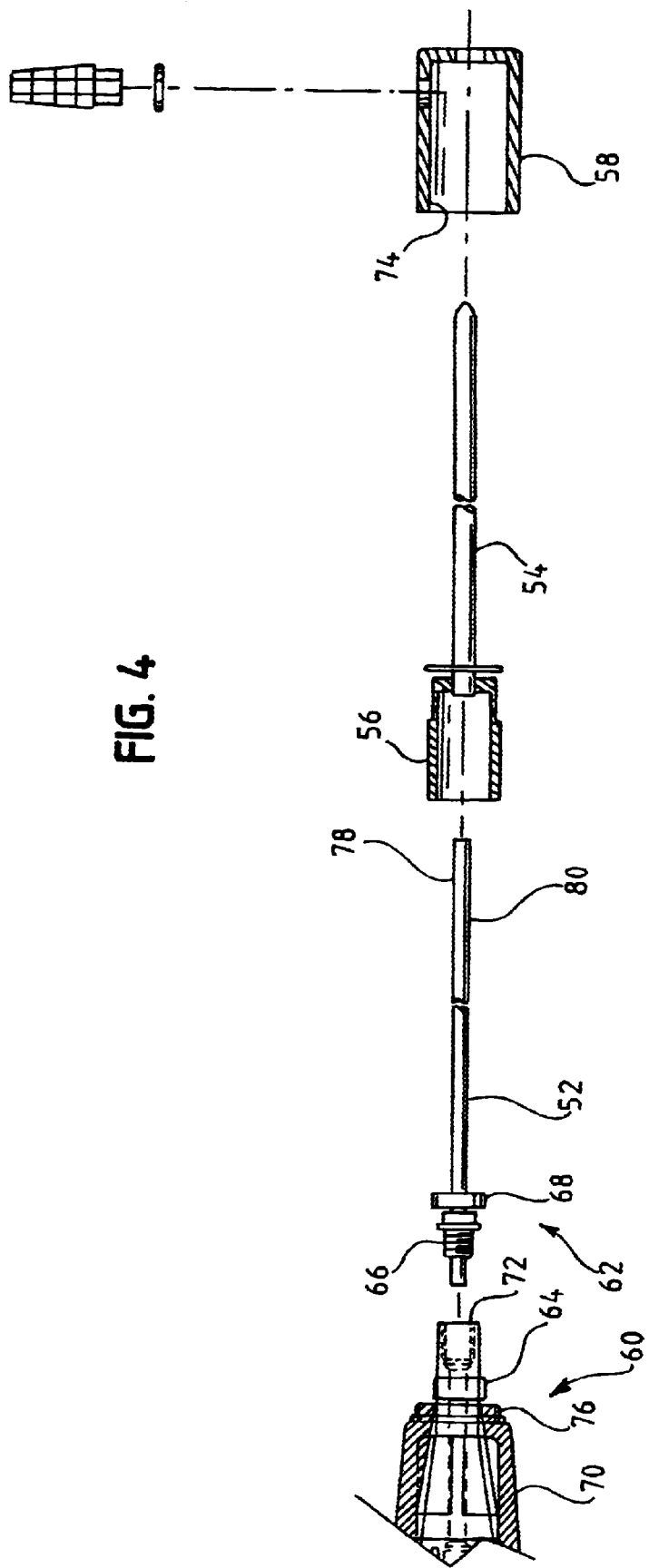

ULTRASONIC PROBE WITH LOW-FRICTION BUSHINGS

FIELD OF THE INVENTION

The field of the invention relates to ultrasonic devices and more particularly to ultrasonic probes used for therapeutic purposes.

BACKGROUND OF THE INVENTION

Ultrasonic probes and probing is known. One use for such devices is in lithotrity (also commonly referred to as lithotripsy). Another use is in liposuction.

Lithotrity is a process for removing concretions, such as calculus stones, within human ducts such as the ureter or kidney. Under the process, a rigid probe is inserted into the body of the subject with a first end juxtaposed against the concretion. An ultrasonic signal is imposed onto the probe from a second end to break up the concretion.

In liposuction, a tip of the rigid probe is inserted under the skin of a patient against the fat of the patient. The ultrasonic signal imposed upon the probe dissolves the fat which may then be carried away by an irrigating fluid.

The ultrasonic signal is typically generated by use of an electrically stimulated ultrasonic motor which may be rigidly attached to the probe. A variable power supply is used to supply a controlling signal to the ultrasonic motor.

The probe used is often hollow and typically made of an impervious material such as stainless steel. A vacuum is often applied to an external end of the hollow tube to draw debris out of the body of a patient. In lithotrity, the tip used to contact and break up calculus stones is fabricated of a harder material than the remainder of the probe.

The length of the probe is usually selected to be an integer multiple of one-half wavelength at the operating frequency. Selecting the length of the probe as a integer multiple of one-half wavelength at the operating frequency (and appropriate selection of tube thickness and coupling components) causes the probe to function as a resonator. The use of the probe as a resonator reduces the net power required for effective operation.

While the use of ultrasonics for lithotrity or liposuction is effective, it is subject to a number of difficulties. For instance, lithotrity and liposuction devices are typically hand-held. To improve operator comfort and reduce an ultrasonic power requirement, the handle of such a device is typically isolated from the ultrasonic probe. The need for isolation between the handle and probe results in a high wear area subject to mechanical failure.

Further, it is often useful to provide a source of irrigation fluid near the tip of the ultrasonic probe. However, locating an irrigation tube near the tip of the probe often results in inadvertent contact between the probes resulting in a damping of ultrasonic energy. In order to improve the effectiveness of ultrasonic devices, a need exists for a means of providing irrigation fluid to a tip of an ultrasonic probe that is not subject to difficulties of prior devices.

SUMMARY

An ultrasonic probe assembly is provided. The probe assembly includes a cannula and an ultrasonic probe disposed within the cannula. The probe assembly further includes a low-friction bushing disposed within the cannula and adapted to maintain the cannula and ultrasonic probe in a relatively fixed longitudinal relationship.

BRIEF DESCRIPTION OF THE DRAWINGS

FIG. 4 depicts an ultrasonic system in accordance with an alternate embodiment of the invention.

DETAILED DESCRIPTION OF A PREFERRED EMBODIMENT

Figure 1:
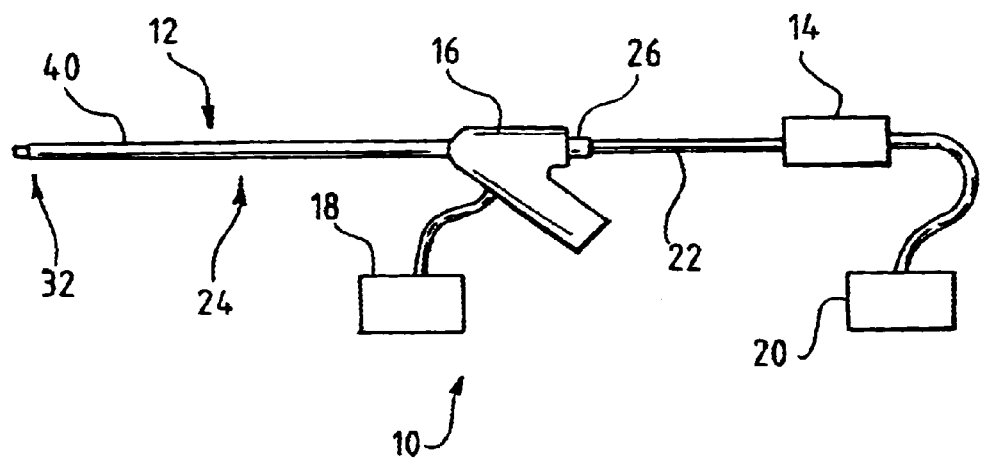
FIG. 1 depicts an ultrasonic system in accordance with an embodiment of the invention.

FIGS. 1 and 4 depict ultrasonic systems 10, 50 in accordance with illustrated embodiments of the invention. Included within the system 10 of FIG. 1 is a probing assembly 24 that may be used as a conduit into the ducts of a patient (not shown) as an endoscope. The system 50 of FIG. 4 may be used for liposuction.

Turning first to the endoscope of FIG. 1, the probing assembly 24 may include an endoscopic probe 12 and ultrasonic probe 22. The endoscopic probe 12 generally includes a cannula 40, a handle 16 and assorted fittings. For example, an appropriate fitting (e.g., a Leuer fitting) 26 is provided through which a number of diagnostic and therapeutic devices may be inserted into the endoscopic probe 12, such as the ultrasonic probe 22 of FIG. 1.

In accordance with the illustrated embodiment, the probing assembly 24 is constructed to facilitate the delivery of ultrasonic energy to a distal end 32 of the probing assembly 24 with improved efficiency. Such improved efficiency is provided by a system which ensures the physical spacing between the probe 22 and surrounding cannula 40, while still providing a passageway for the delivery of irrigating fluid to the distal end 32 of the ultrasonic probe 22.

The ultrasonic probe 22 may be fabricated of stainless steel tubing or of an alloy, such as a titanium alloy. The cannula 40 of the endoscopic probe 12 may also be made of stainless steel.

An ultrasonic power source 14 (e.g., a high-frequency electrical source coupled to a piezoelectric transducer) is shown in FIG. 1 as connected to a proximal end of the ultrasonic probe 22. An aspirator 20 is also shown connected to the ultrasonic probe 22 through the power source 14. The aspirator 20 is provided to aspirate debris and fluids from an operating site through a central passageway of the probe 22.

A source 18 of irrigating fluid is shown connected to a handle 16 of the endoscopic probe 12. The source 18 provides irrigating fluid to a distal tip of the ultrasonic probe 22 through the endoscopic probe 12 (e.g., through the annular space between the cannula 40 and ultrasonic probe 22). At the tip, the irrigating fluid flushes debris and fluids into the central channel of the ultrasonic probe 22. The aspirator 20 pulls the debris and fluids back through the probe 22 and, in turn, into the aspirator 20.

Figure 2:
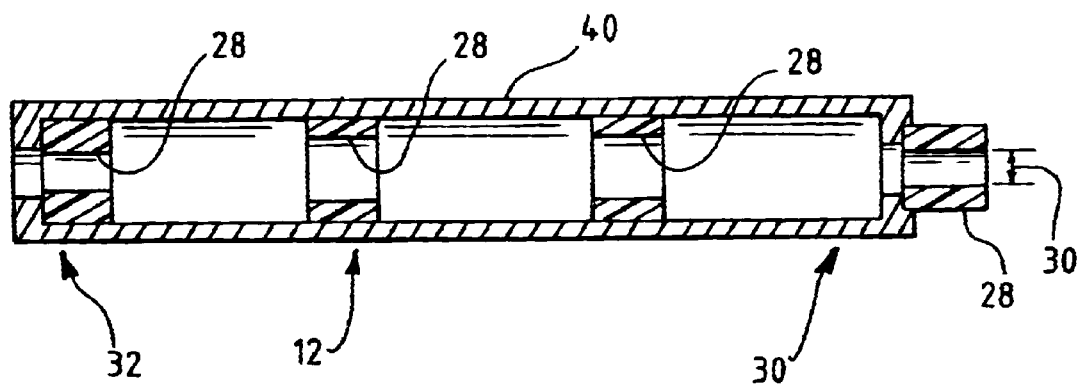
FIG. 2 depicts a cannula of the ultrasonic system of FIG. 1.

FIG. 2 is a cut-away view of a cannula 40 of the endoscopic probe 12. As shown, disposed within the tubing of the cannula 40 may be one or more bushings 28. The bushings 28 may be of any low-friction organic material (e.g., Teflon, PTFE, etc.) that may be formed into the shape of an annulus. An inner diameter 30 of the bushing 28 (FIG. 3) may be provided with a dimension only slightly larger (e.g., 1–2 mils) than an outer diameter of the ultrasonic probe 22. An outer diameter 32 (FIG. 3) of the bushing 28 may be sized to form an interference fit with an inner diameter of the cannula 40.

While FIG. 2 shows four bushings 28, it should be understood that a lesser or greater number of bushings 28 could be used to achieve the advantages of the invention. For example, where the ultrasonic probe 22 is supported on a proximal end 30 by the motor 14, then only a single bushing 28 may be needed on a distal end 32. Alternatively, where the ultrasonic probe 22 is not supported by the motor 14 at a proximal end 30, then two bushings 28 may be required (i.e., one at each end).

Further, the ultrasonic probe 22 may be supported at any number of additional discrete locations within the cannula 40, as shown in FIG. 2. For example, using an operating frequency of the motor 14 and physical characteristics of the probe 22 a set of vibration nodes may be determined for the probe 22. Using such determined information, the bushings 28 may be located at the vibration nodes 78 (or antinodes 80)to further improve the performance of the probing assembly 24.

Figure 3:
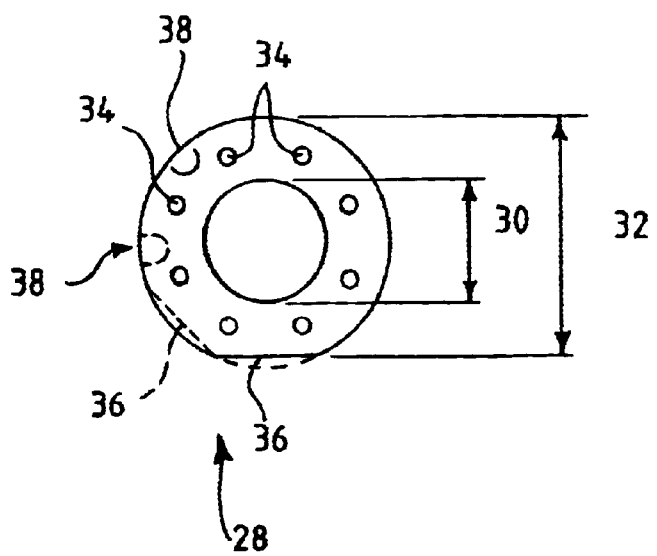
FIG. 3 depicts a bushing used with the cannula of FIG. 2.

FIG. 3 is an end view of a bushing 28 that may be used in the cannula 40 of the endoscopic probe 12 of FIG. 2. As shown, a number of peripheral apertures 34 may be disposed around the annulus of the bushing. The peripheral apertures may provide a passageway from the irrigation source to the distal end 32 of the probing assembly 24.

Under an alternate embodiment, the function of the apertures 34 may be provided by one or more flat spots 36 disposed on an outer peripheral surface of the bushing 28. Alternatively, the flat spot 36 of FIG. 3 may be replaced by one more grooves 38 disposed on the outer surface of the bushing 28.

Turning now to FIG. 4, a ultrasonic system will now be considered in the context of liposuction. A cannula 54 and ultrasonic probe 52 form a probing assembly coupled to an ultrasonic motor 60.

A set of bushings 64, 68 function to isolate the cannula 54 of the probing assembly from the probe 52. As with above examples, the bushings 64, 68 may be fabricated of Teflon or other low-friction materials.

As shown, an ultrasonic probe 52 is coupled to an ultrasonic power source 60. A set of external threads 66 on the probe 52 engages a set of internal threads 72 of the power source 60.

A cannula 54 substantially surrounds the probe 52. An enlarged base forms a hub 56 of the cannula 54 which surrounds the junction between the probe 52 and power source 60.

A set of bushings 64, 68 function to isolate and maintain the cannula 54 in an axially centered position around the probe 52. A first bushing 64 slips over an attachment projection of the motor 60. A second bushing 68 with a smaller inner diameter slips over the probe 52. The hub 56 of the cannula 54 slips over the first and second bushing 64, 68 and allows the cannula 54 to be supported and isolated from the ultrasonic energy of the probe 52. A shroud 58 slips over the cannula 54 and probe 52 and retains the hub 56 of the cannula 54 in contact with an outer housing 70 of the motor 60. The shroud 58, in turn, is retained in position by a set of internal threads 74 which engage a set of external threads 76 located on a shoulder of the motor 60.

The use of the bushings 28, 64, 68 provide a means of stabilizing and controlling the location of the ultrasonic probe 22, 52 within the cannula 40, 54 of the endoscopic probe 12 or liposuction device 50. Since the bushings allow for only a limited lateral motion of the probe, there can be no direct contact and, therefore, no damping of ultrasonic energy due to contact between the probe and cannula.

Further, the use of low-friction bushing materials reduces the mechanical wear between the cannula and probe and the energy required to achieve ultrasonic resonance. The result is an improvement in overall efficiency of the robing assembly.

In a further embodiment, the cannula 54 of FIG. 4 may be provided with a set of internal bushings 28 as shown in FIG. 2. Apertures 34, flat spots 36 or slots 38 may be provided to improve fluid flow within the cannula 54.

The fabrication of ultrasonic probing assemblies with bushings of a low-friction material reduces losses and allows for a smaller ultrasonic motor. The provision of peripheral holes, flat spots or grooves around the annulus of the bushing allows an irrigating fluid to easily pass from a proximal end to a distal end for both carrying away debris and fluids, but also to cool the ultrasonic probe.

A specific embodiment of an ultrasonic probe assembly according to the present invention has been described for the purpose of illustrating the manner in which the invention is made and used. It should be understood that the implementation of other variations and modifications of the invention and its various aspects will be apparent to one skilled in the art, and that the invention is not limited by the specific embodiments described. Therefore, it is contemplated to cover the present invention any and all modifications, variations, or equivalents that fall within the true spirit and scope of the basic underlying principles disclosed and claimed herein.

What is claimed is:

1. An ultrasonic probe assembly comprising:
   a rigid cannula;
   a rigid ultrasonic probe disposed within the cannula; and
   a plurality of low-friction bushings disposed within the cannula at a plurality of spaced-apart locations along a length of the cannula and adapted to maintain the cannula and ultrasonic probe in a relatively fixed longitudinal relationship.

2. The ultrasonic probe assembly as in claim 1 wherein the low-friction bushing further comprises teflon.

3. The ultrasonic probe assembly as in claim 1 wherein the low-friction bushing further comprises PTFE.

4. The ultrasonic probe assembly as in claim 1 wherein the fixed longitudinal relationship further comprises an axial alignment of a longitudinal axis of the ultrasonic probe and a longitudinal axis of the cannula.

5. The ultrasonic probe assembly as in claim 4 wherein the low-friction bushing further comprise an annular shape with a bore of the annulus engaging an outer surface of the ultrasonic probe and an outer surface of the annulus engaging an inner surface of the cannula.

6. The ultrasonic probe assembly as in claim 5 wherein the annulus of the bushing further comprises a plurality of peripheral apertures disposed around the bore of the annulus with a bore of each of the peripheral apertures lying parallel to the bore of the annulus.

7. The ultrasonic probe assembly as in claim 5 wherein the annulus of the bushing further comprises a flat spot disposed on an outer surface of the annulus.

8. The ultrasonic probe assembly as in claim 5 wherein the annulus of the bushing further comprises a plurality of flat spots disposed on an outer surface of the annulus.

9. The ultrasonic probe assembly as in claim 5 wherein the annulus of the bushing further comprises a groove disposed across a width of the annulus.

10. The ultrasonic probe assembly as in claim 5 wherein the annulus of the bushing further comprises a plurality of grooves disposed across a width of the annulus.

11. The ultrasonic probe assembly as in claim 1 wherein the low-friction bushing further comprises a bushing at a distal end of the cannula.

12. The ultrasonic probe assembly of claim 1 wherein the plurality of low-friction bushings further comprises a bushing at a distal end of the cannula and a bushing at a proximate end of the cannula.

13. The ultrasonic probe assembly as in claim 12 wherein the plurality of low-friction bushings further comprises a bushing located at a center of the cannula.

14. The ultrasonic probe assembly as in claim 1 wherein the low-friction bushing further comprises a bushing located at a vibration antinode of the ultrasonic probe.

15. The ultrasonic probe assembly as in claim 1 wherein the low-friction bushing further comprises a bushing located at a vibration node of the ultrasonic probe.

* * * * *